US009717441B2

(12) United States Patent
Soler et al.

(10) Patent No.: US 9,717,441 B2
(45) Date of Patent: Aug. 1, 2017

(54) AUTOMATIC METHOD OF PREDICTIVE DETERMINATION OF THE POSITION OF THE SKIN

(71) Applicant: INSTITUT DE RECHERCHE SUR LES CANCERS DE L'APPAREIL DIGESTIF—IRCAD, Strasbourg (FR)

(72) Inventors: Luc Soler, Wolfisheim (FR); Jacques Marescaux, Scharrachbergheim (FR); Stephane Nicolau, Kehl (DE); Alexandre Hostettler, Strasbourg (FR)

(73) Assignee: INSTITUT DE RECHERCHE SUR LES CANCERS DE L'APPAREIL DIGESTIF—IRCAD (ASSOCIATION REGIE PAR LES ARTICLES 21 A 79 DU CODE CIVIL ET LOCAL ET INSCRITE AU REGISTRE DES ASSOCIATIONS DU TRIBUNAL D'INSTANCE DE STRASBOURG), Strasbourg (FR)

( * ) Notice: Subject to any disclaimer, the term of this patent is extended or adjusted under 35 U.S.C. 154(b) by 0 days.

(21) Appl. No.: 14/770,471

(22) PCT Filed: Mar. 3, 2014

(86) PCT No.: PCT/FR2014/050454
§ 371 (c)(1),
(2) Date: Aug. 26, 2015

(87) PCT Pub. No.: WO2014/132008
PCT Pub. Date: Sep. 4, 2014

(65) Prior Publication Data
US 2016/0000355 A1    Jan. 7, 2016

(30) Foreign Application Priority Data
Mar. 1, 2013 (FR) ..................... 13 51855

(51) Int. Cl.
*G06K 9/00* (2006.01)
*A61B 5/055* (2006.01)
(Continued)

(52) U.S. Cl.
CPC ............ *A61B 5/055* (2013.01); *A61B 5/1127* (2013.01); *A61B 5/1128* (2013.01);
(Continued)

(58) Field of Classification Search
USPC ........ 382/100, 103, 106–107, 128–132, 162, 382/168, 173, 181, 199, 219, 232, 254,
(Continued)

(56) References Cited

U.S. PATENT DOCUMENTS 8,747,382 B2 * 6/2014 D'Souza .............. A61B 5/1135
604/500
9,387,347 B2 * 7/2016 Maurer, Jr. .............. A61N 5/10
(Continued)

FOREIGN PATENT DOCUMENTS

WO    2005/032647 A2    4/2005
WO    2010/113052 A1    10/2010

OTHER PUBLICATIONS

Hostettler A et al.: "A real-time predictive simulation of abdominal viscera positions during quiet free breathing" Progress in Biophysics and Molecular Biology, Pergamon Press, Oxford, GB, vol. 103, No. 2-3, Dec. 1, 2010 (Dec. 1, 2010), pp. 169-184, XP027546512, ISSN: 0079-6107 [retrieved on Sep. 29, 2010] cited in the application the whole docume.*
(Continued)

*Primary Examiner* — Seyed Azarian
(74) *Attorney, Agent, or Firm* — Young & Thompson

(57) ABSTRACT

An automatic process of predictive determination of the position and movements of the skin of a subject in a zone of interest, with the subject breathing freely or in an assisted
(Continued)

manner, includes preliminarily acquiring multiple configurations of the skin profile in axial planes, at given successive times, in different respiratory positions, and for each axial plane, constructing at least one deformable digital model starting from different skin profiles, then noting, in a repetitive manner, the actual position of a point on the skin at the level of each axial plane, whose position is significantly modified during inhalation and exhalation phases, and providing, essentially in real time, a simulation of the skin profile in each axial plane, as a function of the actual position noted, and an evolving three-dimensional representation of the skin at the level of the zone of interest, by interpolation between the different axial planes.

20 Claims, 21 Drawing Sheets
(21 of 21 Drawing Sheet(s) Filed in Color)

(51) Int. Cl.
*A61B 5/11* (2006.01)
*A61B 5/113* (2006.01)
*A61B 6/02* (2006.01)
*G06T 7/11* (2017.01)
*G06T 7/12* (2017.01)
*G06T 7/136* (2017.01)
*A61B 5/00* (2006.01)
*A61B 6/00* (2006.01)
*A61B 90/00* (2016.01)

(52) U.S. Cl.
CPC .............. *A61B 5/1135* (2013.01); *A61B 6/02* (2013.01); *G06T 7/11* (2017.01); *G06T 7/12* (2017.01); *G06T 7/136* (2017.01); *A61B 5/0077* (2013.01); *A61B 5/7275* (2013.01); *A61B 6/52* (2013.01); *A61B 2090/3937* (2016.02); *A61B 2090/3954* (2016.02); *A61B 2090/3958* (2016.02); *A61B 2576/00* (2013.01); *G06T 2207/30088* (2013.01); *G06T 2207/30204* (2013.01)

(58) Field of Classification Search
USPC ....... 382/256, 274, 276, 286–289, 305, 312, 382/291; 378/4, 8, 21; 600/301, 340; 1/1; 604/500
See application file for complete search history.

(56) References Cited

U.S. PATENT DOCUMENTS

2009/0010514 A1* 1/2009 Kimura ............ G01R 33/56509
382/131
2009/0175406 A1* 7/2009 Zhang .................... A61B 5/113
378/8
2012/0004518 A1* 1/2012 D'Souza .............. A61B 5/1135
600/301

OTHER PUBLICATIONS

Hostettler A et al.: "A real-time predictive simulation of abdominal viscera positions during quiet free breathing" Progress in Biophysics and Molecular Biology, Pergamon Press, Oxford, GB, vol. 103, No. 2-3, Dec. 1, 2010 (Dec. 1, 2010), pp. 169-184, XP027546512, ISSN: 0079-6107 [retrieved on Sep. 29, 2010] cited in the application the whole document.

Hostettler A et al.: "Bulk modulus and volume variation measurement of the liver and the kidneys in vivo using abdominal kinetics during free breathing", Computer Methods and Programs in Biomedicine, Elsevier, Amsterdam, NL, vol . 100, No. 2, Nov. 1, 2010 (Nov. 1, 2010), pp. 149-157, XP027287835, ISSN: 0169-2607 [retrieved on Sep. 15, 2010] cited in the application the whole document.

International Search Report, dated Jun. 3, 2014, from corresponding PCT application.

* cited by examiner

AUTOMATIC METHOD OF PREDICTIVE DETERMINATION OF THE POSITION OF THE SKIN

FIELD OF THE INVENTION

This invention relates to the field of techniques of imagery and exploratory representations of subjects, more particularly human subjects, in particular in real time or almost-real time, and it has as its object an automatic process for predictive determination of the skin position of a subject and deformations/movements of the latter because of breathing.

BACKGROUND OF THE INVENTION

Currently, within numerous medical contexts, respiratory movements constitute a parameter that it is necessary to take into account.

For example, in radiotherapy, the planning target volume (PTV), which is not modified during treatment, is deliberately overestimated in such a way as to take into account movements of the target tumor that are linked to unknown movements due to breathing. If this makes it possible to ensure complete irradiation of the tumor, this increases at the same time the irradiation of healthy tissue, which is not desirable for the patient's health.

Within the context of percutaneous punctures in interventional radiology, to reach his target, the radiologist asks the patient to hold his breath in a respiratory position that is similar to that of the tomodensitometric medical image, MRI, or echographic image that is used for highlighting the target. Consequently, the duration of the operation is clearly longer than if the position of the tumor were perfectly known.

These two illustrative examples explain the necessity for developing precise methods for simulation of the movement of the organs induced by breathing.

The respiratory movement has been considered for a long time as a perfectly cyclical movement, and consequently, it has often been characterized by a single variable representing, for example, the volume of air breathed in by the patient, or else a cutaneous marker positioned on the thorax. This approach is well known by one skilled in the art in the field in question.

In practice, this is not the case, as has been stated in particular in the article "A Real-Time Predictive Simulation of Abdominal Viscera Positions During Quiet Free Breathing"—"Simulation prédictive en temps-réel des positions des viscères abdominaux durant la respiration libre non forcée"—A. Hostettler et al., Progress in Biophysics and Molecular Biology, 103 (2010), pp. 169-184, ELSEVIER. In this article, in particular multiple markers are provided per axial plane of interest to monitor the movements of the skin, using a large number of optical markers or projection of structured light, for the purpose of studying or simply knowing the position of a patient's skin, without seeking to make a skin movement model.

Actually, in this article, the authors implemented a real-time monitoring of the movement of the skin at the level of the mid-sagittal plane using 8 optical markers (see Section 2.2), illustrating that, since the respiratory movement is primarily due to the combined action of the diaphragm and intercostal muscles, within the framework of free breathing, the action of these two effector muscles has not taken place in phase, and the amplitude of their respective movement changes over time. Consequently, it is not possible to model the respiratory movement or that of a target in the viscera using a single variable. For the same position of a cutaneous marker, a localized target in the viscera can have multiple significantly different locations.

Some of these methods for simulation of the movement of organs induced by breathing take into account the non-cyclical nature of the respiratory movement: the real-time knowledge of the position of the patient's skin is then obligatory for predicting the movement of the organs.

Actually, the skin position can be used to guide a digital model that predicts the position of the structures of interest located in the abdominal cavity, the thoracic cavity, or else the abdominal wall, such as, for example, in the above-mentioned article, in which the complete anterior surface of the abdomen and the thorax is used to guide the model, either via the use of the structured light, or via a number of cutaneous markers.

In addition, by way of the document "Bulk Modulus and Volume Variation Measurement of the Liver and the Kidneys In Vivo Using Abdominal Kinetics During Free Breathing"—A. Hostettler et al., Computer Methods and Programs in Biomedicine, 100 (2010), 149-157, furthermore, a process for determining variations in position and shape of the liver and kidneys during free breathing of a human subject is known, using a deformable model of the shape of the diaphragm to monitor the patient's skin. This document essentially goes back over the teaching that was already disclosed in the previously-cited document.

Although so-called "motion capture" methods exist today that make it possible to provide a real-time modeling of the skin of a moving subject, they require, however, all of the important material resources, making their implementation incompatible with an installation within an operating room (for example, the product that is known under the name "alignRT" of the ©vision RT Company). In addition, these known methods in general provide only an estimation or measurement of a fractional zone of the patient's skin and not the entirety of a zone of interest (for example, over essentially 360° and over a significant length in the cranio-caudal direction).

In concrete terms, this surface data is difficult to obtain: during breathing, the skin moves nearly throughout and in different directions; only a portion of the surface that is in contact with the table remains immobile. Moreover, in numerous applications, it is necessary to monitor the skin position with an error that should not exceed on the order of one millimeter.

More specifically, essentially three different methods are currently known that are able to provide an exploitable result, but have all of the major drawbacks, namely:

a) Projection of structured light, monitored by camera and reconstruction of the surface of the skin:

In this case, a projection of structured light should be carried out from multiple sources in such a way as to cover the entire surface of the patient's skin. This poses a coverage problem at the junction of multiple projections. There should also be numerous cameras that make it possible to monitor the movements of the skin so as to ensure the complete visualization of these projections. A robust image processing algorithm should be used to calculate in real time the skin position that is then described as a cloud of more or less ordered points. Finally, this cloud of points should most often be resampled in such a way as to make it usable.

Be that as it may, with the patient lying on a table, this method makes it possible to locate only the portion of the skin that is visible with the cameras and on which the structured light is projected.

b) Monitoring by markers glued on the patient's skin and calculation of skin position by interpolation methods:

This method represents a simplification of the preceding method by reducing the number of points monitored in a significant way. Although faster, it keeps the same limits: the cameras should be numerous enough to monitor all of the visible markers. As a result, only the portion of the skin that is visible to the cameras and on which the markers are placed can be monitored. Finally, the interpolation will be less precise than the preceding method.

c) Monitoring of electromagnetic markers glued on the patient's skin (such as, for example, the Aurora system (filed name), developed by the NDI Company) and calculation of the skin position by interpolation methods:

In this case, there is no need for a camera, but the interpolation problems are similar. Moreover, the precision of the measurement of the position provided by the electromagnetic markers is lower than the preceding methods (from 1 to 5 mm), with the measurement error being in addition potentially increased by the presence of metal objects in the measuring fields.

This last limitation added to the current limitation of the number of simultaneously usable markers as well as to the frequency limited to 50 Hz actually makes it difficult to implement this method in the clinical routine.

Taking the preceding into account, the primary object of the invention is to propose a solution for modeling movements of the skin of a human subject that provides a reliable and precise three-dimensional simulation of at least one zone of interest, which evolves in real time and only requires a minimum number of measurements and limited processing power.

SUMMARY OF THE INVENTION

For this purpose, the invention has as its object an automatic process of predictive determination, for example in the form of a digital simulation, of the position and movements of the skin of a human subject or an animal in a zone of interest located at the level of the thorax and/or the abdomen, with said subject being elongated (for example on his/its back), and breathing freely or in an assisted manner, with said process consisting, in a preliminary manner, in acquiring or determining multiple positions and configurations of the profile of the skin in predetermined, consecutive, axial planes that are essentially perpendicular to the craniocaudal axis (of the subject/of the table of the imager) and distributed along this axis at determined locations, at given successive times, during the respiratory movement, process characterized in that it consists, during a preliminary treatment phase and for each axial plane in question, in constructing at least one deformable digital model of the profile of the skin in said axial plane from data pertaining to different skin profiles that are acquired or determined previously, in then noting, in a repetitive manner, the actual position of a point or a specific point zone on the skin of the subject at the level of each of the above-mentioned axial planes, of which the position is modified in a significant manner during the respiratory movement (series of inhalation and exhalation phases), and in providing, essentially in real time, a simulation of the profile of the skin in each axial plane, as a function of the actual (current) position noted for each point or specific point zone 4 and in exploiting the corresponding deformable digital model, as well as an evolving three-dimensional representation of the skin at the level of the zone of interest, by interpolation between the different above-mentioned axial planes.

The basic principle of the invention rests on the exploitation of the surprising observation made by the inventors that, in the case of a human subject breathing normally, freely, or in an assisted manner, a reliable and precise three-dimensional modeling of the skin of the subject (at the level of the region of the thorax and the abdomen), making possible a real-time prediction of the movements of the skin, could be carried out by noting in a continuous manner only the data pertaining to the movement and to the position of a restricted number of points selected on the skin, and by exploiting a modeling of the movement of the skin on a limited number of consecutive axial planes, created from data acquired previously.

More specifically, highlighting and monitoring in real time the position of a single point on the skin makes it possible—by exploiting a deformable model created from multiple axial profiles of the skin acquired at different respiratory positions but at the same geographic position and in a given axial plane and comprising this point—to predict the position and the shape of this same profile, themselves modified over time by the respiratory movements over time, based on the subject's breathing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be better understood using the description below, which relates to two embodiments, provided by way of nonlimiting examples and explained with reference to the accompanying schematic drawings, in which.

DETAILED DESCRIPTION OF THE INVENTION

Figure 1A:
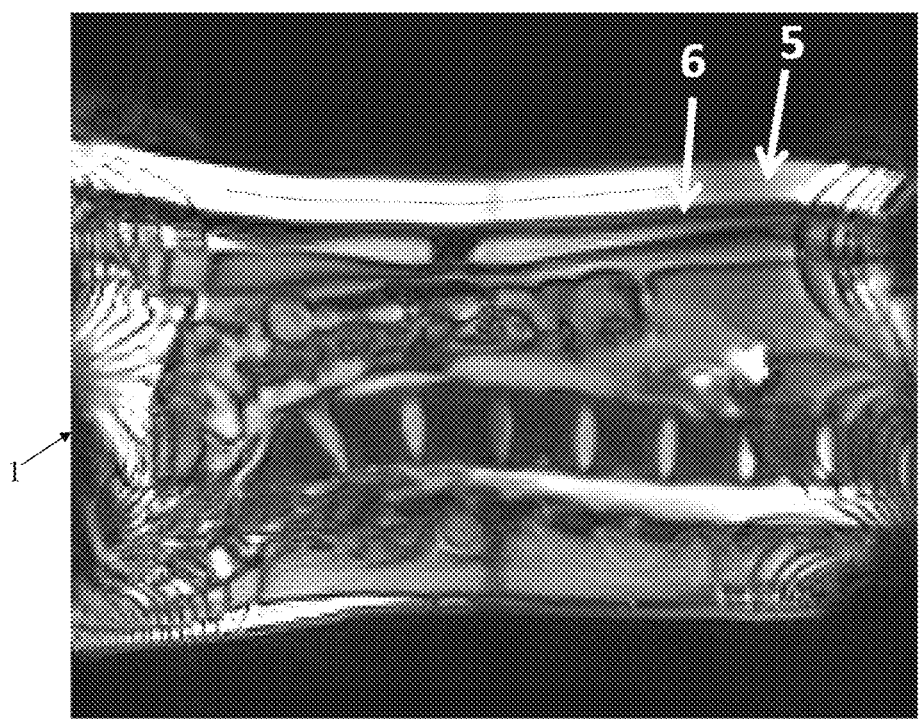
FIGS. 1A to 1C are views, obtained by MRI, according to the mid-sagittal plane of a human subject provided with a wire marker according to the invention, respectively in the exhaled state (FIG. 1A), in the inhaled state (FIG. 1B), and by superposition of the different positions taken by the marker (by means of its median curve) in the inhalation and exhalation phases (FIG. 1C)
Figure 1B:
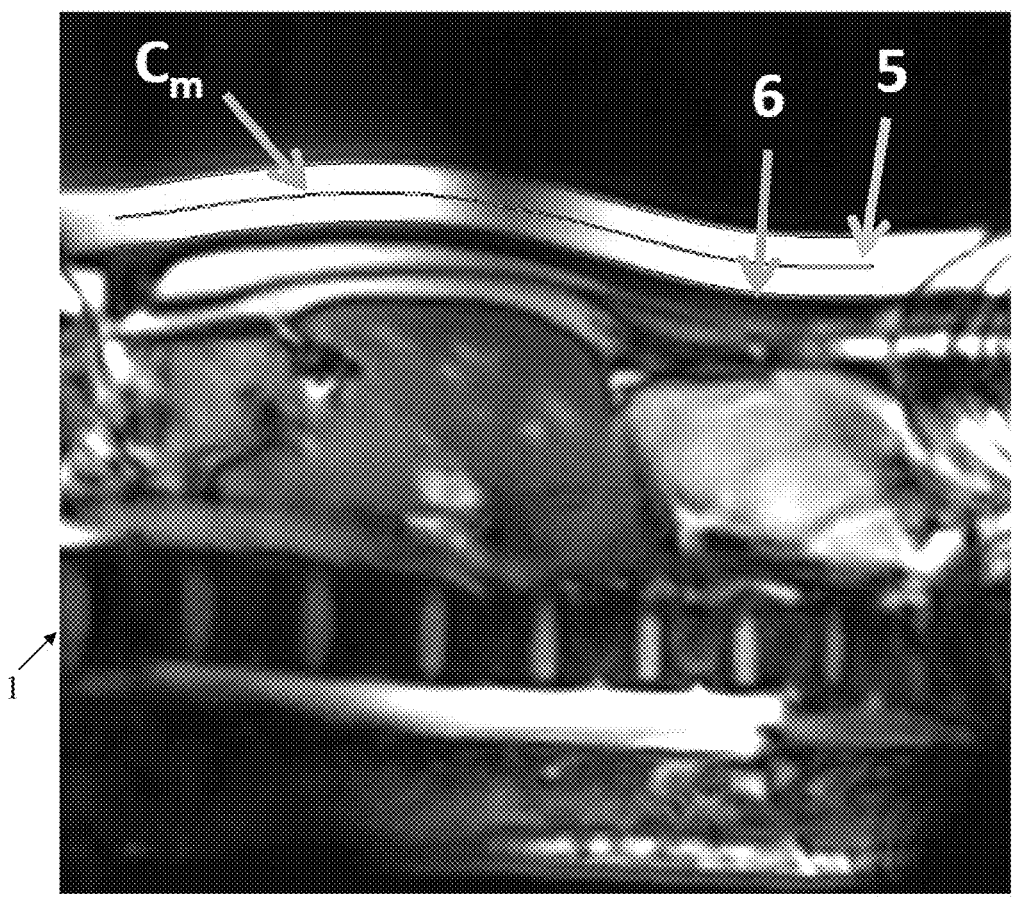
Figure 1C:
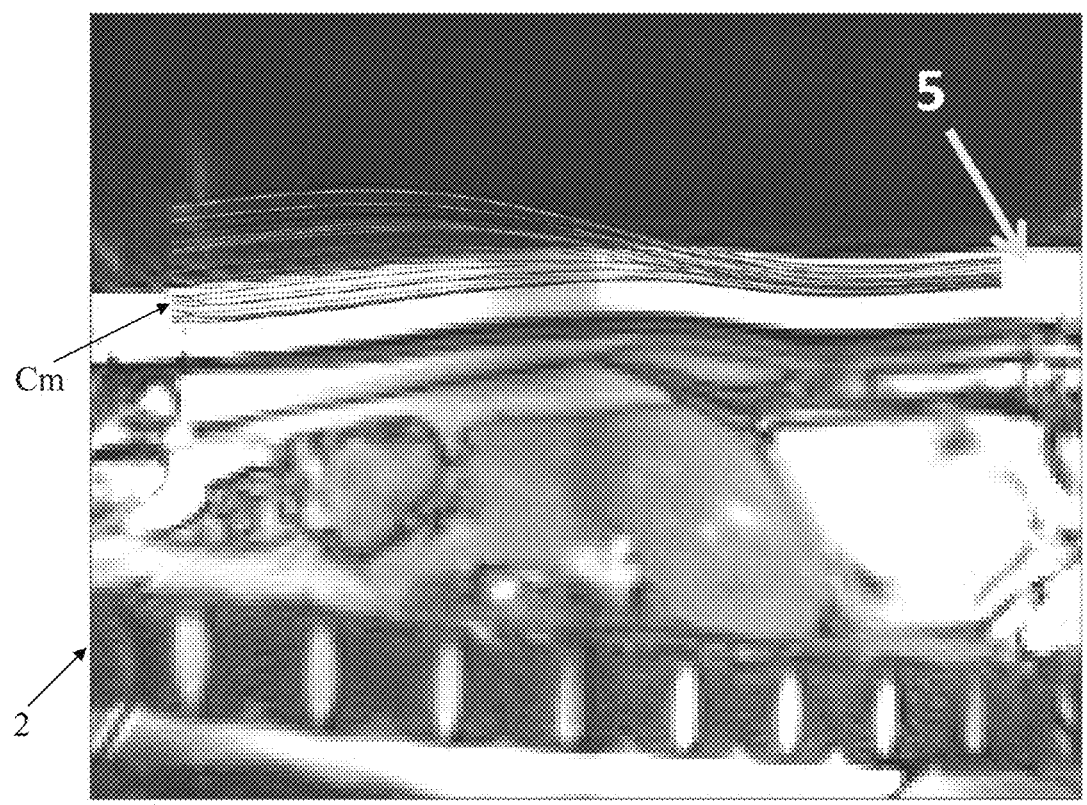

The invention relates to an automatic process for predictive determination, for example in the form of a digital simulation, of the position and movements of the skin 2 of a human subject 1 or an animal in a zone of interest located at the level of the thorax and/or the abdomen.

Within the framework of a preferred embodiment of the invention, it is considered that the subject 1 is stretched on his/its back and breathes freely or in an assisted manner.

In agreement with the general principles and the essential characteristics of the invention, the process consists, in a preliminary manner, in acquiring or determining multiple positions and configurations of the skin 2 in at least two positions of the respiratory cycle, in such a way as to be able to observe a respiratory movement whose amplitude is essentially similar to the amplitude corresponding to the breathing. These acquisitions are made using a conventional 3D imager of the CT-scan type. In addition, these acquisitions are to cover the zone of interest of which it is subsequently desired to be able to simulate the movement.

Once these 3D images have been acquired, the next step is to extract from them the position of the skin, which, for example, by applying a simple operator for processing the thresholding-type image, is common practice and can be carried out easily by one skilled in the art. Once the position of the skin has been extracted and calculated in each 3D image, the intersections of this non-planar surface with a certain number of axial planes Pa selected consecutively along the craniocaudal axis of the patient are calculated.

It is possible to use only two 3D acquisitions, i.e., corresponding, for example, respectively to the exhaled position and an inhaled position of the patient, and a series of curve pairs (representing the skin profiles), corresponding respectively to the skin profile of the patient in exhalation and in inhalation in each axial section Pa, is then obtained.

The invention then provides for constructing an independent digital model for each axial section, corresponding, by way of simple example, to a linear interpolation between the position of the exhalation curve and the position of the inhalation curve.

Thus, by monitoring the position in a repetitive manner from a point or a specific point zone 4 of the skin 2 of the subject 1 at the level of each of the above-mentioned axial planes Pa, and of which the position is modified in a significant manner during the respiratory movement, it is possible to provide, essentially in real time, a simulation 3' of the skin profile in each axial plane Pa by exploiting the previously-described deformable digital model. The invention then makes it possible to create an evolving three-dimensional representation 2' of the skin 2 at the level of the zone of interest by interpolation between the simulated position of the skin at the level of the different axial planes Pa.

One possible effective way of monitoring a point for each modeled axial section of the patient's skin (skin profile) may be to choose to position all of the axial points to be monitored on the same plane, which can be the mid-sagittal plane. In this case, it is necessary only to monitor the movement of the profile of the skin at the level of the mid-sagittal plane to know the position of all of the points that must be monitored in each axial plane, since these points constitute the profile of the skin at the level of the mid-sagittal plane.

The invention is described below in a more detailed manner, in connection with a particular embodiment, illustrated by the accompanying figures and having variants for certain aspects.

As above, it is considered that the subject 1 is stretched on his/its back and breathes freely or in an assisted manner.

The process consists, in a preliminary manner, in acquiring or determining multiple positions and configurations of the profile 3 of the skin 2 in predetermined consecutive axial planes Pa, essentially perpendicular to the craniocaudal axis X and distributed along this axis at determined locations, at given successive times, in at least two positions of the respiratory cycle, in such a way as to be able to observe a respiratory movement whose amplitude is essentially similar to the amplitude corresponding to normal breathing. The determination of the position of the skin at the level of the axial profiles can be carried out simultaneously for multiple profiles at the same time, if the acquisition device allows it.

In accordance with the invention, this process also consists, during a preliminary phase, for each axial plane Pa in question, in constructing at least one deformable digital model of the skin (profile) starting from data pertaining to the different skin profiles 3 that are acquired or determined previously. Next, in a repetitive manner, the actual current position of a point or a specific point zone 4 of the skin 2 of the subject 1 is noted at the level of each of the above-mentioned axial planes Pa (preferably highlighted using a marker 5 that is visible in the imagery process that is used), whose position is modified in a significant manner by the respiratory movement. Finally, there is provided, essentially in real time, a simulation 3' of the profile of the skin in each axial plane Pa, based on the actual position noted and by exploiting the corresponding deformable digital model, but also optionally an evolving three-dimensional representation 2' of the skin 2 at the level of the zone of interest, by interpolation between the different axial planes Pa.

In an advantageous manner, and so as to facilitate the monitoring of the movement of the skin and to increase its precision, it is desirable that the points or specific point zones 4 of the skin 2, whose actual position is monitored over time, be placed in a parallel plane that is close to or merged with the mid-sagittal plane MSP of the subject 1, by preferably being spaced mutually by a distance on the order of one centimeter.

However, it may also be provided that the points or specific point zones 4, whose actual position is monitored over time, are distributed along the craniocaudal axis by being aligned or not, with their number advantageously being at least equal to approximately 10 and their spacing of at most 5 cm in the direction of the above-mentioned axis.

In accordance with the invention, the process preferably consists in, for each axial plane Pa in question, generating essentially in real time a curve 3', which shows the profile 3 of the skin 2 in the axial plane Pa in question, by applying a deformation to a base curve Cb of the axial profile of the skin, for example by moving at least certain points spaced on the base curve, based on the measured position of a point 4 on the skin 2 of the subject 1 located in the axial plane Pa in question.

The base curve that is used preferably corresponds to the axial profile of the skin noted in the maximum exhalation state of the subject 2.

Figure 2A:
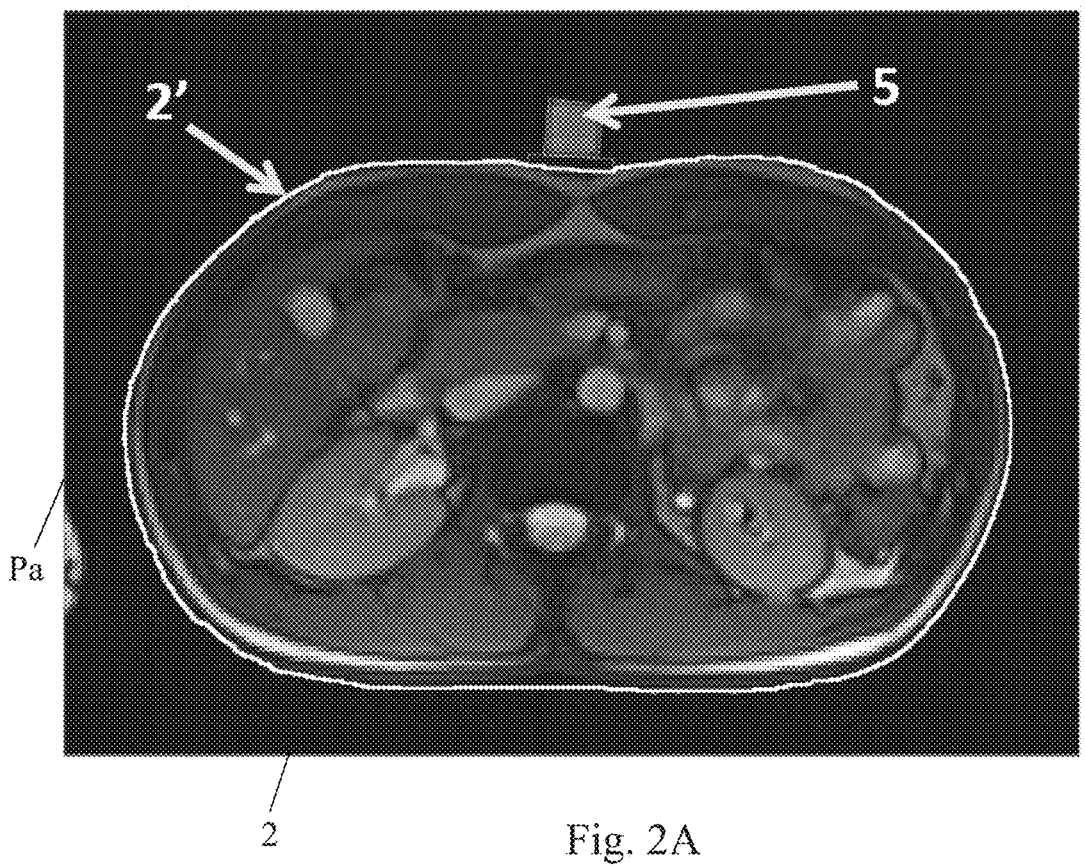
FIGS. 2A to 2D are views, obtained by MRI, along an axial plane at the level of a zone of interest of a human subject provided with the marker of FIG. 1, illustrating the profile of the skin that is determined in the exhaled state (FIG. 2A) and the inhaled state (FIG. 2B), with the calculation of the reference curve from two curves of profiles extracted from FIGS. 2A and 2B (FIG. 2C), and the generation of a deformation field from pairs of points (pairing of points) belonging to two skin profile curves of FIGS. 2A and 2B (FIG. 2D)
Figure 2B:
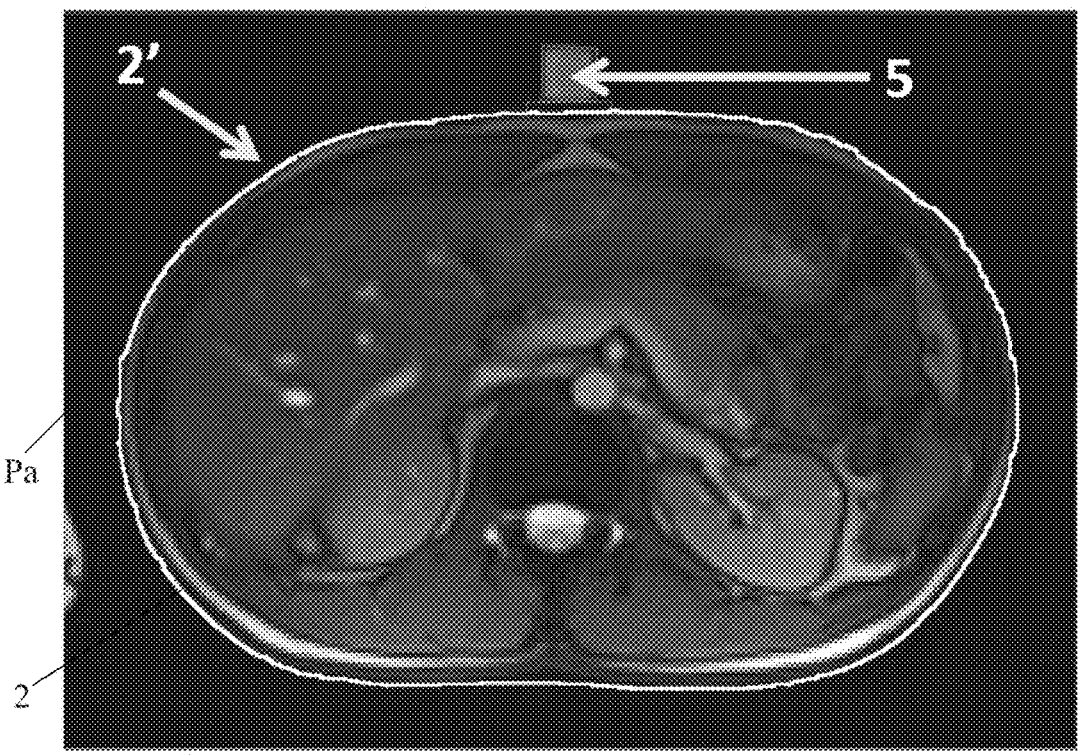
Figure 2C:
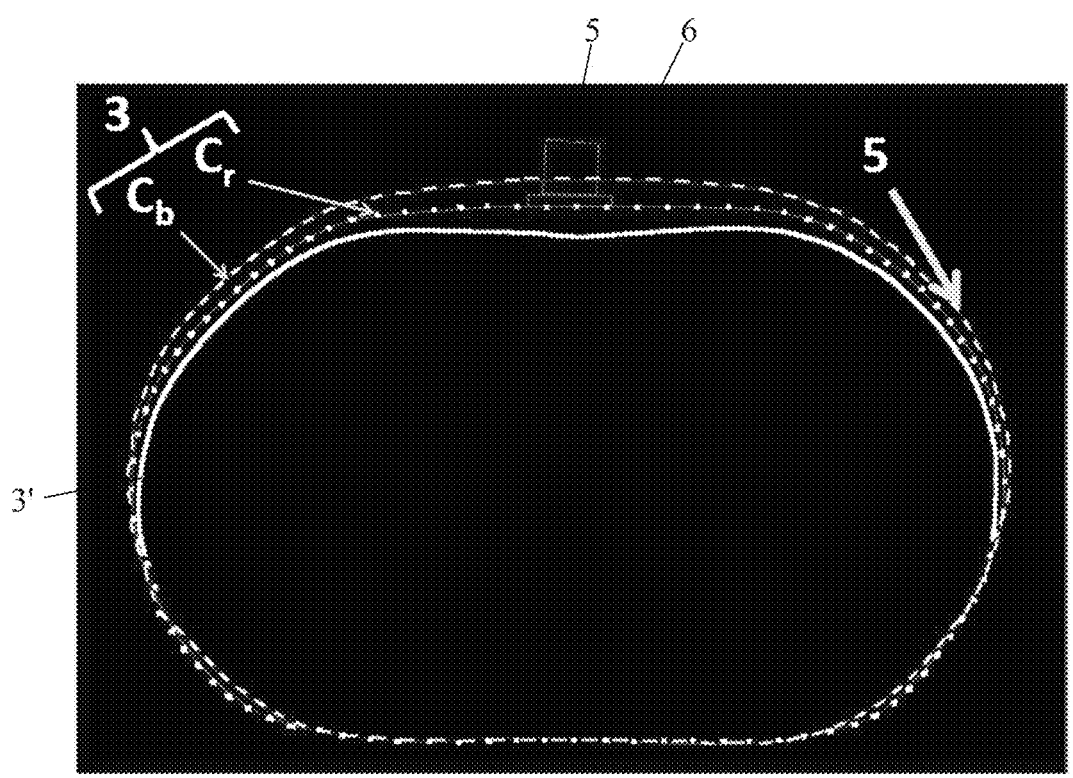
Figure 2D:
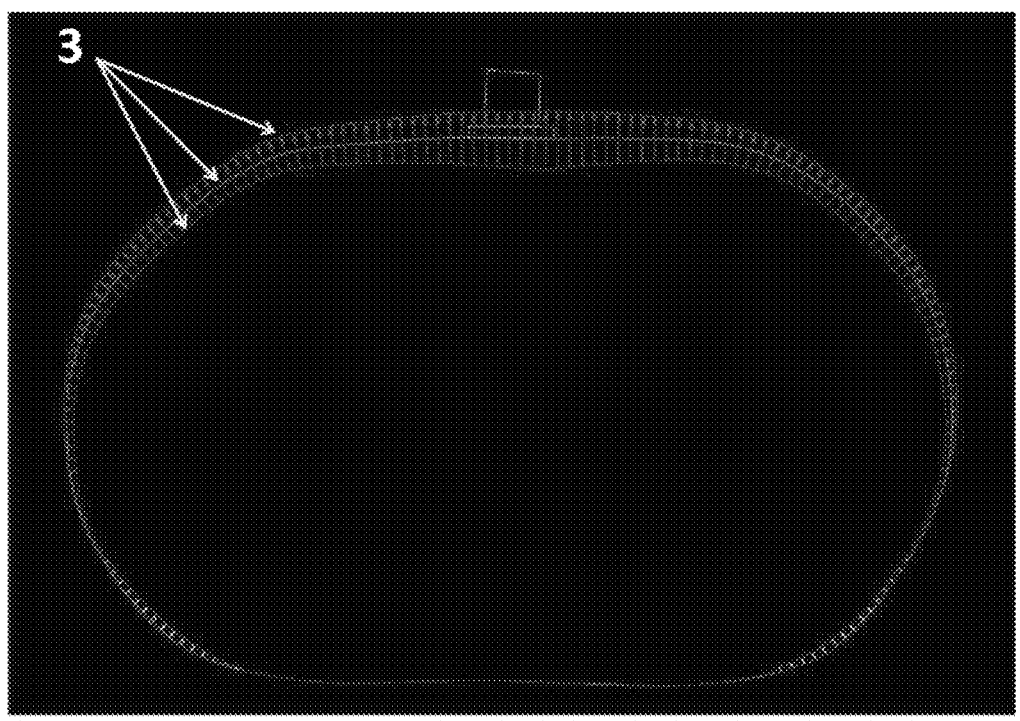
Figure 3:
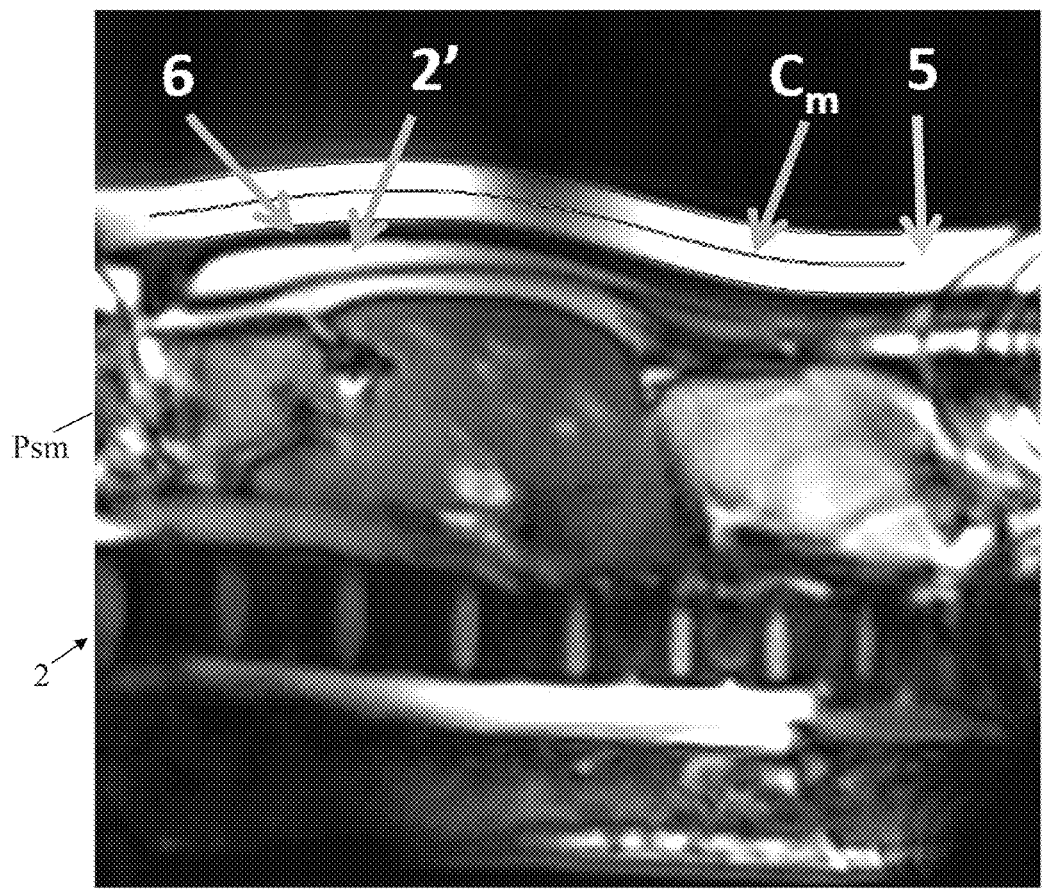
FIG. 3 is a view that is similar to that of FIG. 1B with an illustration of the median curve of the marker.
Figure 4A:
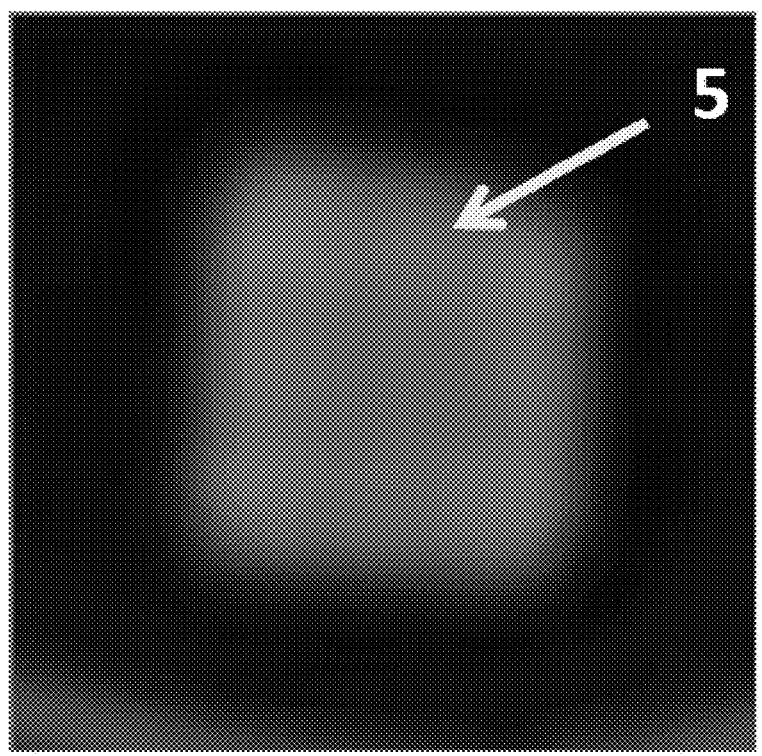
FIGS. 4A to 4C are detail axial cutaway views of the marker illustrating the stages for determination of the contours and the slope of the marker.
Figure 4B:
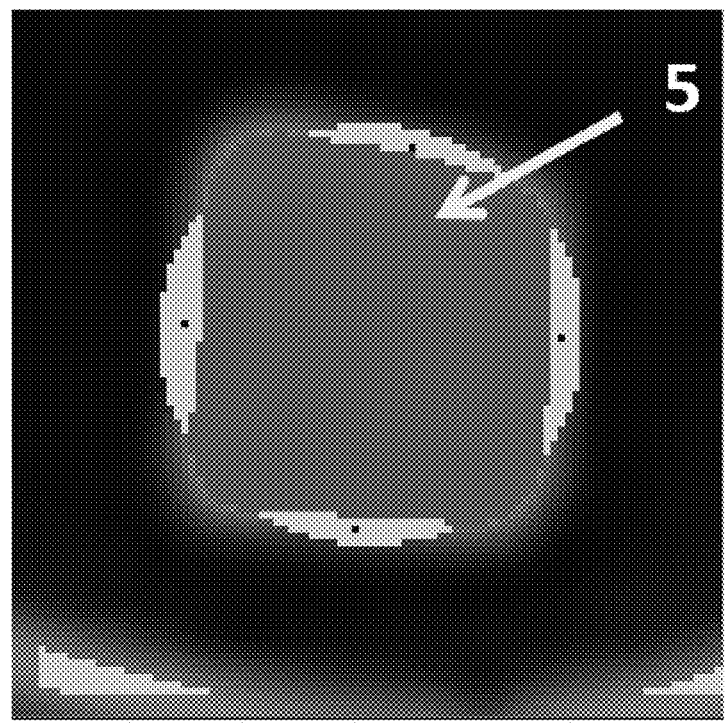
Figure 4C:
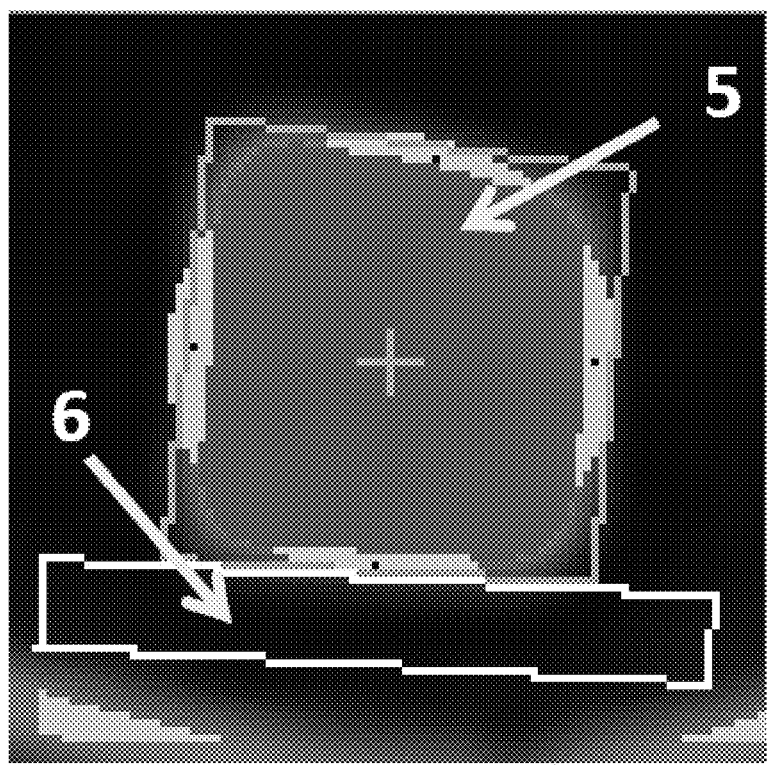

Advantageously, and as FIG. 2D illustrates by way of example (for inhalation and exhalation positions), each deformable digital model of a skin profile, respectively associated with one of the predetermined axial planes Pa, is obtained by pairing points in an essentially radial direction, in the axial plane Pa in question, between at least two shapes or configurations that are significantly different from the curve of the skin profile, corresponding to at least two different respective states of the respiratory movement of the subject.

In accordance with another characteristic of the invention, specifying the preceding embodiment and illustrated by FIGS. 2A to 2D, each deformable digital model of the skin profile, associated with one of the predetermined axial planes Pa, is obtained by generating a reference curve Cr located mid-way between the two skin profile curves corresponding to the end inhalation and exhalation states to determine the intersection points, with the two above-mentioned curves, of a normal to the reference curve Cr and passing through a point of this curve, for a number of points spaced along the latter, and to assemble in an ordered manner these pairs of intersection points to constitute a deformation field corresponding to the movement of the skin 2 in the axial plane Pa in question between the two above-mentioned end states, as a function of the respiratory state of the subject 1.

The above-mentioned points of the curve Cr are spaced enough so that the normals do not cross before intersecting the two axial profiles of the skin.

As indicated previously, the three-dimensional model of overall simulation of the skin consists of a number of elementary axial models that are two-dimensional and independent of the skin, established in consecutive axial planes PA along the craniocaudal axis.

In practice, once the skin is segmented in the images corresponding respectively to the end inhalation and exhalation positions of the subject (FIGS. 2A and 2B), each axial model can be established by executing the following four operating stages (see FIGS. 2C and 2D):

1) Creation of a reference curve Cr located exactly mid-way between the two curves corresponding to the two above-mentioned end positions. This stage can be carried out by using a distance chart corresponding to the difference between the image mask relative to the position of the skin in the inhaled state and the image mask relative to the position of the skin in the exhaled state.

2) Resampling the axial reference curve Cr in such a way as to obtain a set of consecutive points that are spaced in a regular manner.

3) Generation of a normal to the reference curve Cr at the level of each point of this resampled curve.

4) Determination of two intersection points corresponding to the intersection of this normal with the curves of the inhaled and exhaled states that frame it. A set of vectors that are normal to the curve Cr and that thus represent a deformation field reflecting the movement of the surface of the skin in a given axial plane Pa between the two original positions of the different respiratory states is then obtained.

Thus, by repeating this operation for all of the consecutive axial sections, an axial model of the respiratory movement is obtained all along the craniocaudal axis; each set of data resulting from a 2D acquisition makes possible the construction of a local axial model of the patient's skin. Taking into account the variation of the shape of the skin of a conventional subject, the generation of axial models of the skin that are separated from one another by approximately 1 cm makes it possible to obtain by interpolation a reliable and precise three-dimensional model of the patient's skin at the level of the zone of interest.

So as to take into account the hysteresis phenomenon of the movement of the skin during breathing, it is provided within the framework of the process according to the invention to construct two deformable digital models of axial profiles of the skin in each axial plane Pa, namely a model for the inhalation phases and a model for the exhalation phases, and to detect the type of respiratory phase in progress during the production of simulated curves 3' of a skin profile in the different axial planes Pa by means of a specific sensor or by evaluating the direction of movement of the points 4 by considering individually their variations of position relative to their preceding positions.

According to a first variant embodiment, the positions of the specific points 4 on the skin 2 are noted in real time by means of an optical sensor device, in particular with a laser, with or without preliminary installation of optical markers on the patient's skin 2 in the locations of specific points 4, with the latter advantageously being selected in such a way as to obtain a significant modification of their spatial position during the respiratory movement of the subject.

To facilitate the monitoring of the sagittal profile of the skin that corresponds to the concatenation of the different axial points, points 4 on the skin 2 whose movements are taken into account within the framework of the process as initial parameters, the positions of these points 4, located in the mid-sagittal plane MSP of the subject 1 and in the predetermined axial planes Pa, are determined by means of at least one marker 5, preferably a continuously elongated marker, resting directly or indirectly on the skin 2 of the patient 1, conforming in shape to the local surface of the skin 2 and placed in the mid-sagittal plane MSP.

Alternatively, the markers 5 that are used consist of electromagnetic-type markers, such as, for example, miniature coils, resting directly or indirectly on the skin 2, if necessary with a known spacing relative to the latter.

Thus, the specific points 4 on the skin 2 are each highlighted by means of a marker 5 that is particularly readily visible in the imagery process that is used, with these specific points 4 being advantageously located in such a way that their spatial position is modified significantly during the respiratory movement of the subject.

As FIGS. 1 to 4, 6 and 7 show, the marker 5 that is used consists of a flexible and elongated body, made of a material that is particularly readily visible in the imagery system that is used, extending at least over the length of the zone of interest in the direction of the craniocaudal axis X, exhibiting a cross-section of determined minimal size and shape and located at a determined distance from the skin 2 of the subject 1, by resting on a strip 6 of a material that is flexible and essentially invisible in the imagery system that is used.

Knowing the dimensions of the marker 5 and those of the material strip 6 and for the purpose of facilitating the reliable highlighting of the position of the marker 5, the process can advantageously consist in determining and noting, in the sagittal plane, the curve Cm corresponding to the median axis of the elongated marker 5, for example formed by the series of different centers of gravity in the cross-section of said marker 5, and/or in the different axial planes Pa in question, the local centers of gravity of said marker 5, and in determining the positions of specific points 4 on the skin 2 of the subject 1 whose movements are taken into account, by exploiting the data pertaining, on the one hand, to this curve Cm or to these local centers of gravity, on the other hand, to the cross-section and to the cross-sectional dimensions of the marker 5, and finally, to the thickness of the intermediate material strip 6.

In accordance with a preferred practical implementation of the invention, as shown in the accompanying figures, it may be provided that, when the imagery process to which the subject 1 is subjected is based on magnetic resonance, the elongated marker 5 consists of a bar formed by water gel, with a square or rectangular cross-section and a sufficient length to cover at least the zone of the subject whose movements induced by the breathing of said subject 1 are to be monitored (zone of interest).

In this context, the segmentation of the skin in sagittal images obtained by magnetic resonance is advantageously carried out by exploiting the very good visibility of the marker 5 in the MRI images and its contrast relative to the textile strip 6 by means of which it rests on the skin of the subject (the thicknesses of said marker and said strip being known data).

More precisely, this sagittal segmentation phase of the skin can be broken down into four primary stages, namely:

1) A 2D working image that is oversampled and created from the original 2D image (taken on the subject) by implementing a cubic interpolation (this stage increases the precision of the determination of the position of the marker 5). In practice, and taking into account geometric deformations and distortions that affect the 2D MRI images (at the level of the two opposite sides of the ends of the explored zone—see, for example, FIG. 3), only the central part of the initial images is exploited (approximately 60%).

2) Taking into account differences in contrast between consecutive 2D+t images, it is advantageous to determine a threshold value corresponding to the position of the marker 5. Then, in each vertical straight line of the different images, the first string of consecutive pixels having a length that is at least greater than approximately 80% of the thickness of the marker 5 is sought, and the center of the marker 5 is then calculated along each vertical straight line (making it possible to determine the position of the marker along this straight line). The best threshold value corresponds to the one that minimizes the mean distance between the simulated position of the marker and the position extracted, by segmentation, from the original images.

3) The parts of the elongated marker 5 that are not continuous are then located, and the trace of the elongated marker is modified locally by extrapolating the uniform portions of the marker located on both sides of the discontinuous part.

4) An operation for smoothing positions of the consecutive centers of gravity of the marker is carried out in such a way as to correct the segmentation errors due to local information gaps (the use of the center of gravity makes it possible to limit the influence of the effect of partial volume).

Likewise, the segmentation of the marker 5 can be carried out in the axial planes Pa that are provided for the acquisition of 2D+t images by executing the following four operating stages:

1) The search for the location of the marker 5 with a square cross-section, for example, is limited to a search zone defined manually at the beginning of the procedure and then centered automatically by being based on the preceding position of the center of the marker.

2) The best threshold value that makes it possible to obtain at least 80% of the theoretical surface of the cross-section of the marker is sought (pixels whose gray value is less than the threshold value are sought).

3) As soon as the mask showing the cross-section of the marker is found, its center of gravity is calculated by using a known algorithm for calculating the barycenter.

4) The slope of the marker is then evaluated starting from the preceding mask by carrying out, for example, the following operations: determination of the four disk portions of the larger disk centered on the center of gravity of the marker (FIG. 4B); determination of the centers of gravity of these four disk portions (CG1, CG2, CG3, CG4); determination of the horizontal and vertical slopes of the marker by approximation starting from segments connecting, on the one hand, the points CG1 and CG3 and, on the other hand, the points CG2 and CG4.

Finally, the segmentation of the skin in the 2D+t axial images is carried out by using the data pertaining to the position of the marker 5 provided previously.

This axial segmentation can be carried out by executing the following four operating stages (see FIGS. 5A to 5D):

1) A binary mask corresponding to the threshold of the original image is calculated.

Figure 5A:
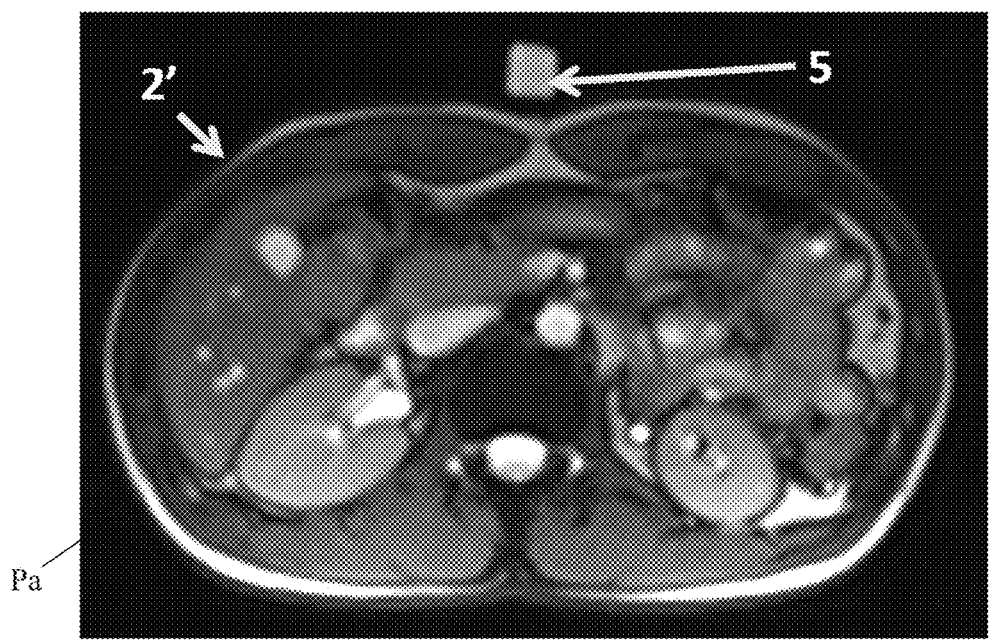
FIGS. 5A to 5D are axial cutaway views illustrating the stages of segmentation and extraction of the skin profile.
Figure 5B:
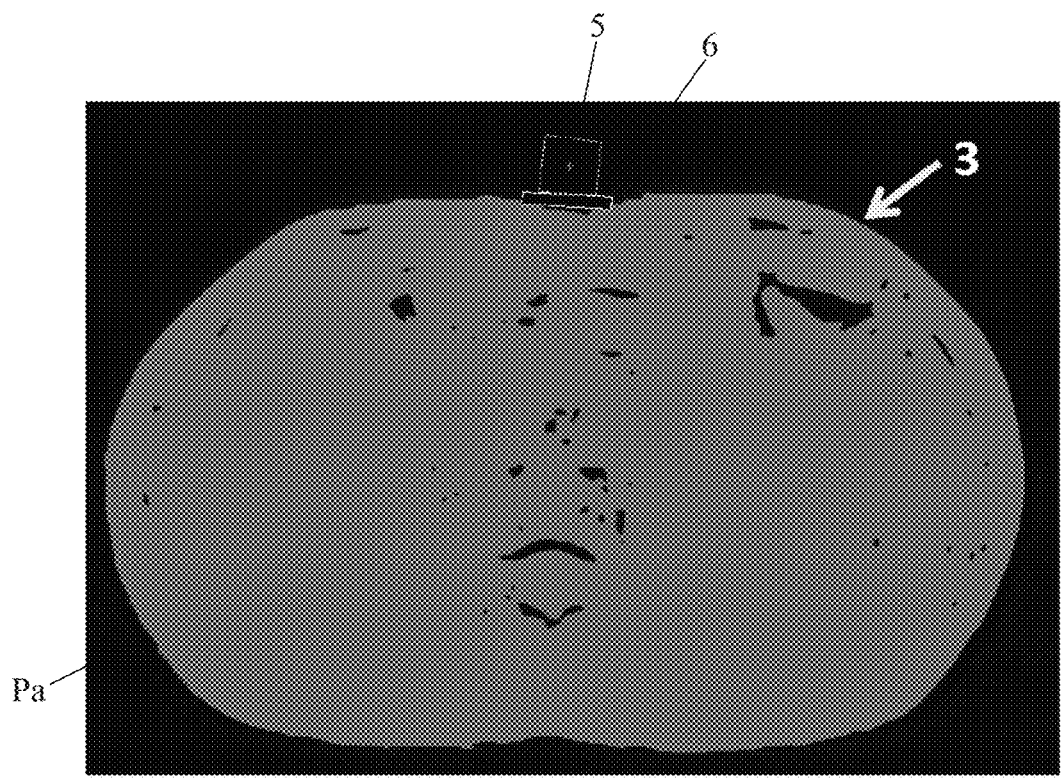
Figure 5C:
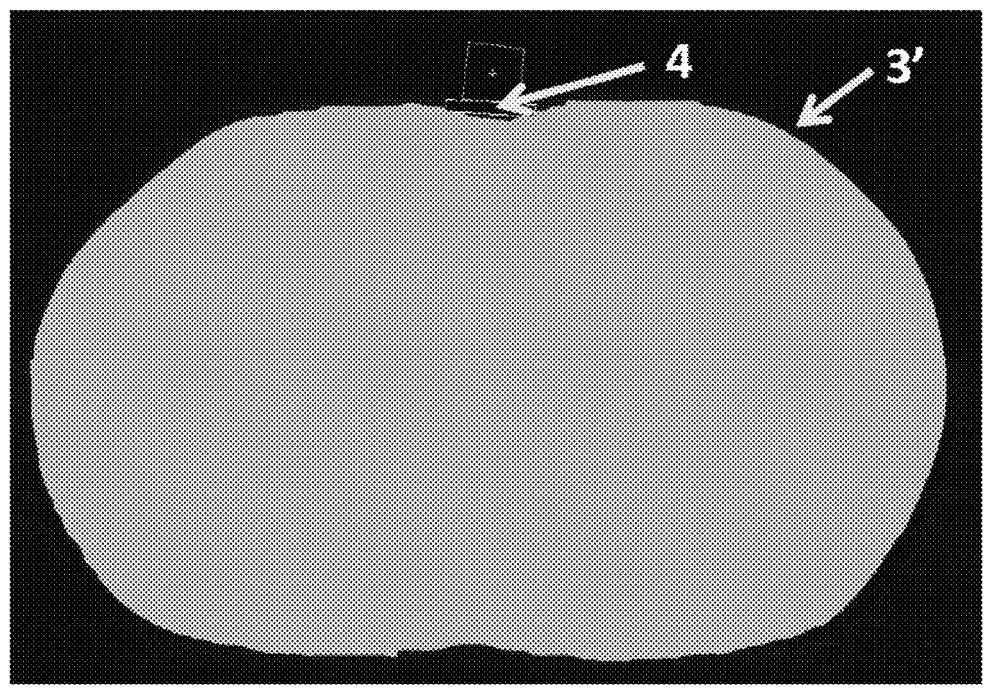
Figure 5D:
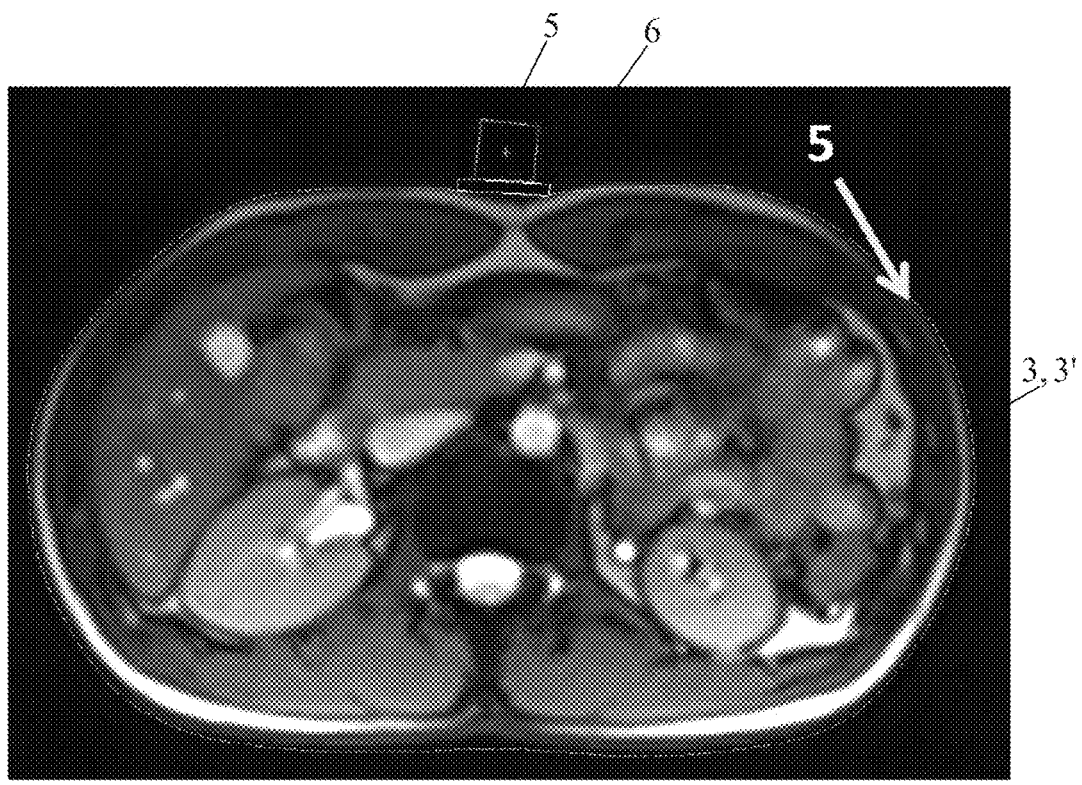

2) Only the largest connected elements of the mask are preserved, and the mask is filled (FIGS. 5B and 5C).

3) The curve corresponding to the peripheral limit of the mask is extracted. Then, this curve is smoothed and completed to remedy the errors and information gaps in the original image.

4) The curve corresponding to the position of the skin is corrected close to the marker 5, knowing the distance between the center of the marker and the skin.

As already mentioned previously, and so as to take into account the hysteresis affecting the skin between the inhalation and exhalation phases, it is recommended according to the invention to construct a different simulation model of the skin as a function of the respiratory cycle phase (inhalation and exhalation).

For this purpose, the curves illustrating the positions of the marker 5 should be classified in two categories: one of which relates to the inhalation phase and the other to the exhalation phase.

Figure 6:
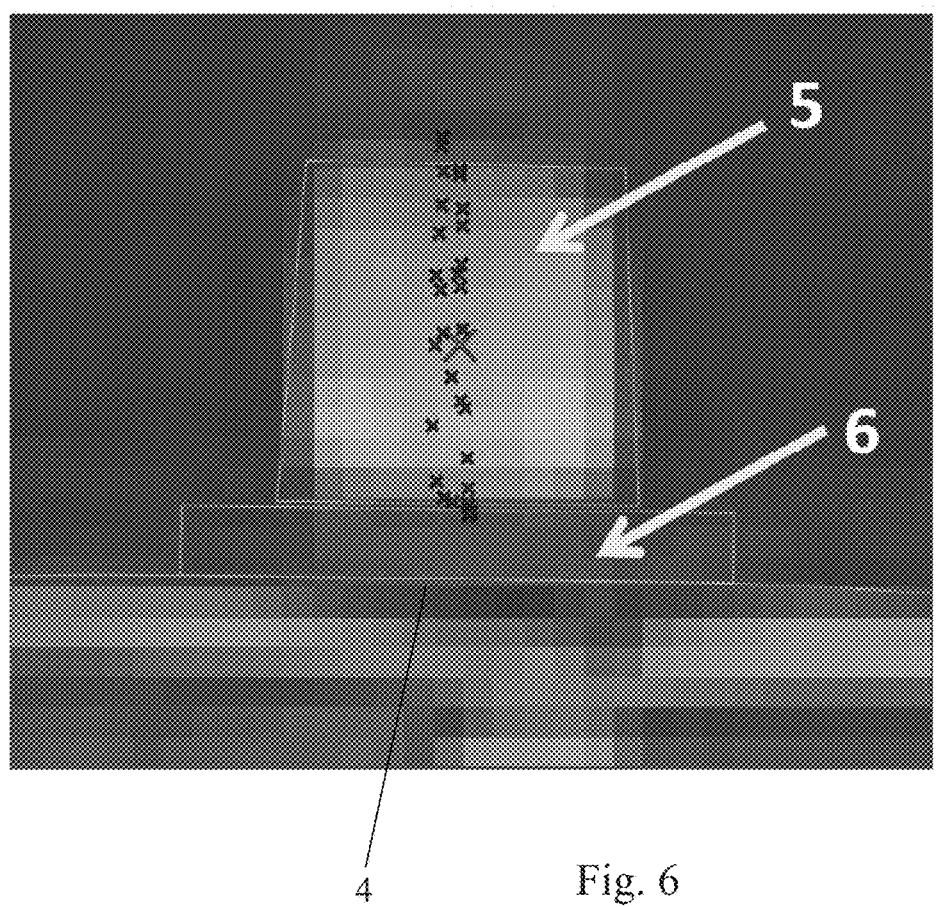
FIG. 6 is a detail axial cutaway view of the marker and its immediate environment, obtained by superposition and illustrating different positions of the center of gravity of the marker and the hysteresis between the positions taken during the inhalation and those taken during the exhalation.
Figure 7A:
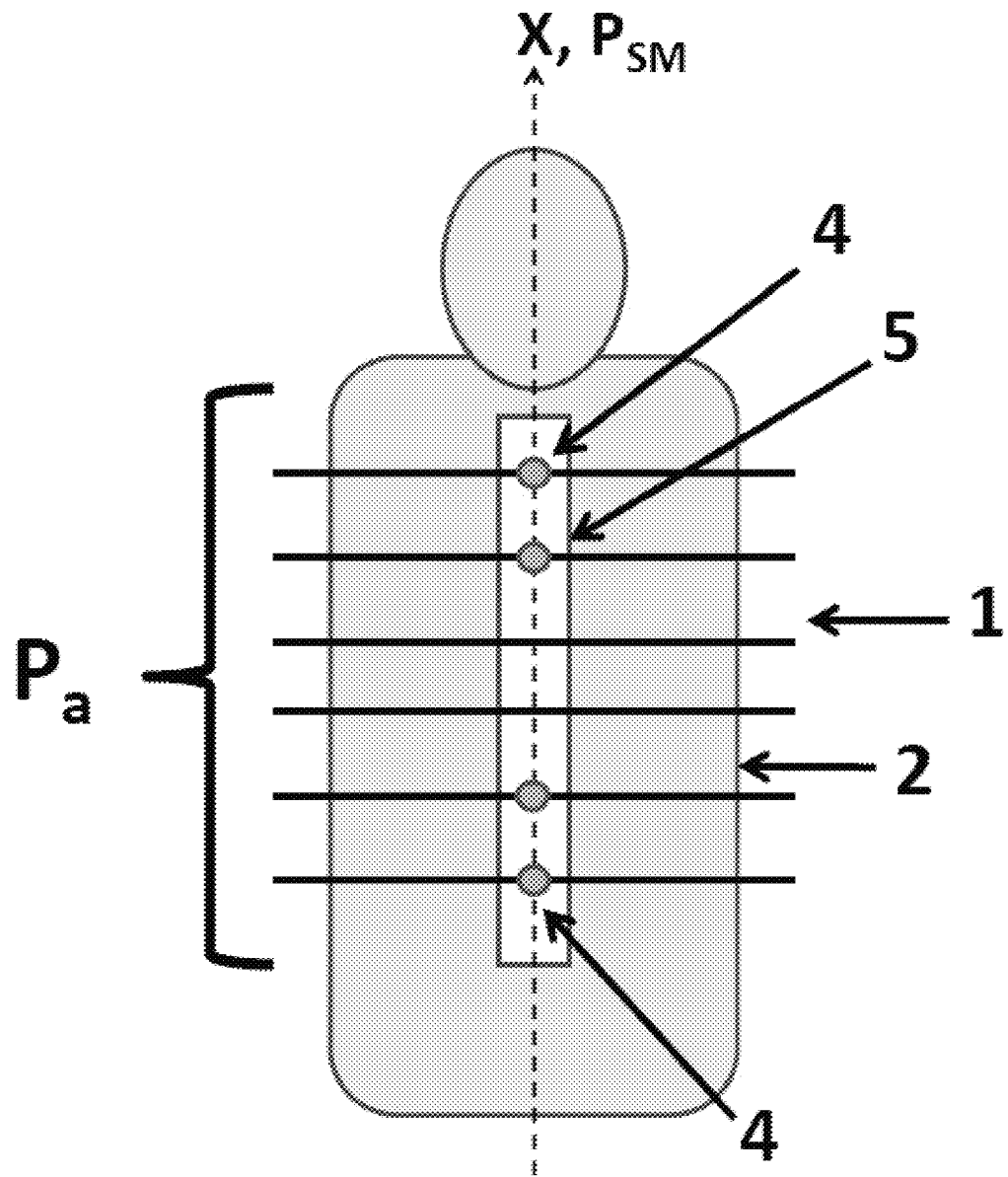
FIGS. 7A and 7B are schematic representations, respectively from the top and side, of the torso and the head of the human subject equipped with a marker according to the invention for monitoring the respiratory movements.
Figure 7B:
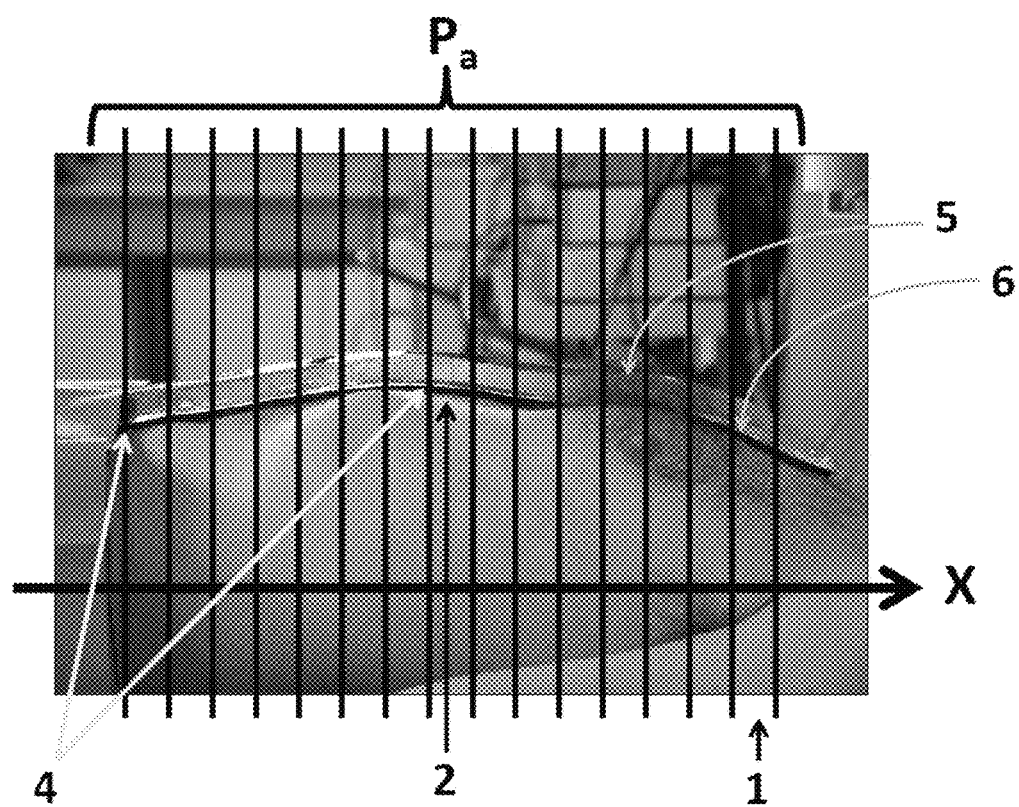
Figure 8A:
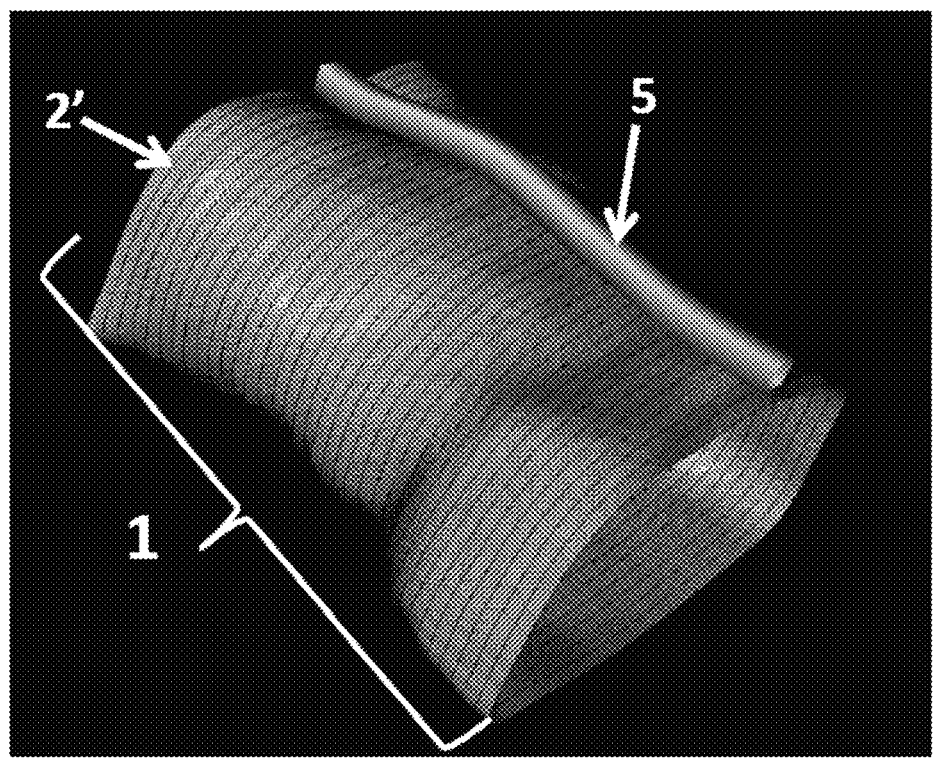
FIGS. 8A to 8C are representations of a three-dimensional digital simulation of the zone of interest of a human patient, controlled with breathing, obtained and used within the framework of the invention, with FIGS. 8B and 8C simultaneously showing views acquired by the imagery in particular planes.
Figure 8B:
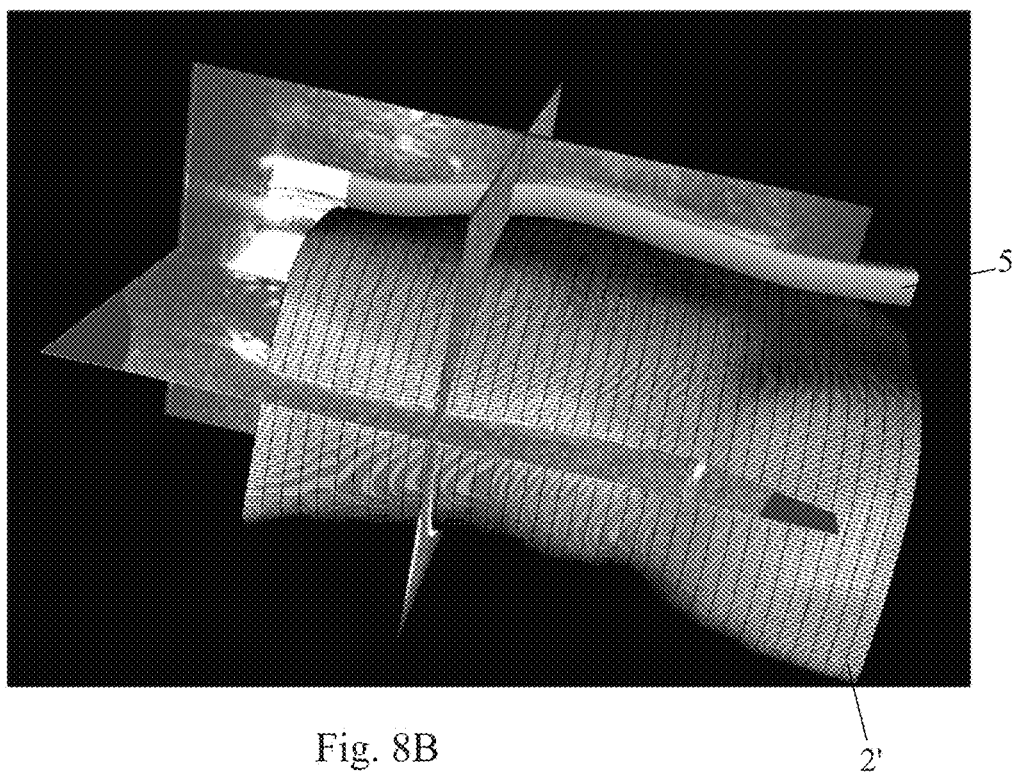
Figure 8C:
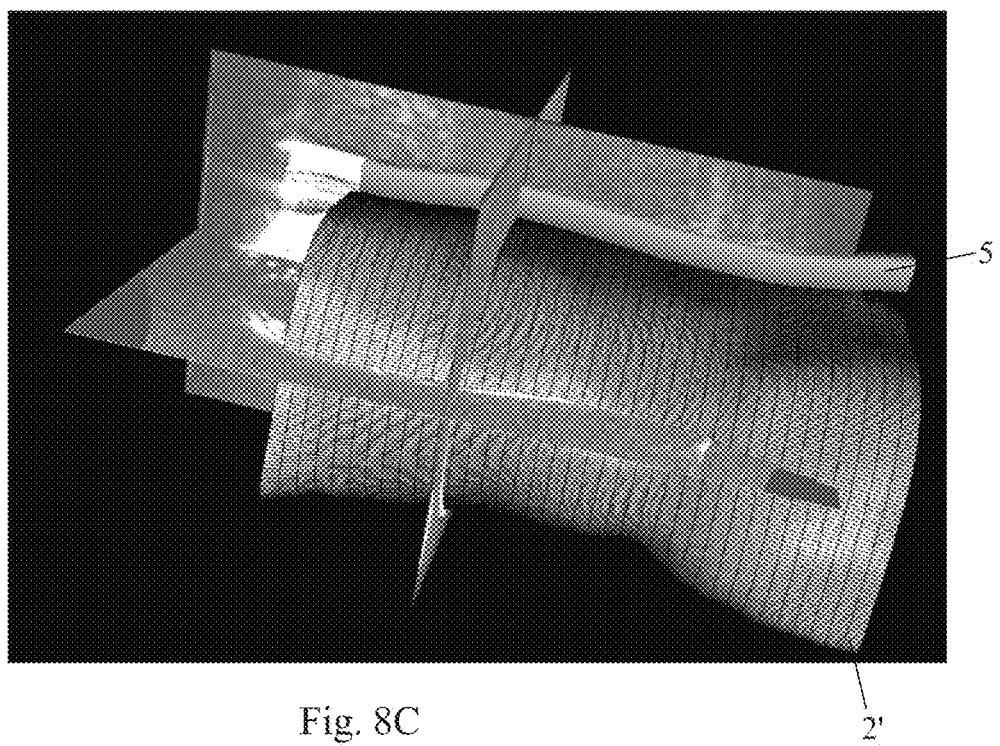

The hysteresis effect is maximal at the end of the inhalation phase and at the beginning of the exhalation phase, and the discrimination of the curves is trivial except for the end inhalation state (see FIG. 6).

So as to be able to distinguish the positions of the marker in this critical state, it is advantageously possible to exploit simultaneously the position of the center of the marker and the curvature of the skin around the marker (the inventors noted that the lateral position of the marker changed because of the modification of the curvature of the skin).

Within the framework of a preliminary acquisition and processing phase of the process according to the invention, the curves showing the profile 3 of the skin 2 in spaced axial planes Pa that are predetermined and at different times of the inhalation and exhalation phases can be obtained in different ways.

Thus, these curves can be:
- extracted, by sampling along these axial planes, from three-dimensional representations of the surface of the skin 2 at the level of the zone of interest, acquired in advance and obtained by highlighting and monitoring the skin by means of markers (electromagnetic, optical, or others) attached to the skin or by means of structured light projected on the skin;
- extracted, by application of a segmentation technique, from three-dimensional representations obtained by an imagery process based on magnetic resonance or tomodensitometry;

extracted, by segmentation, from 2D+t-type images made in said axial planes Pa and obtained by an imagery process based on magnetic resonance or tomodensitometry.

Within the framework of an advantageous medical application of the results provided by the invention, the evolving three-dimensional representation 2' of the skin 2 at the level of the zone of interest is exploited in connection with at least one three-dimensional image of the abdomen, for carrying out a predictive simulation in real time of the positions of the organs and/or viscera of the abdominal cavity during normal free-breathing phases of the subject 1, by implementing, for example, the teaching of the publication cited in the introductory part of this description.

Thus, thanks to the invention, it is possible to make available a three-dimensional simulation evolving in real time of the skin of a patient by continuously noting only the positions of a limited number of points on the skin, i.e., by limiting the necessary treatment resources and limiting the necessary zone that is highlighted while providing sufficient precision for medical applications.

A practical implementation of the invention made it possible to reach a precision of 1 mm and a refresh rate of the simulation at a frequency of 80 Hz.

In addition, by comparative evaluations, the inventors have been able to estimate that the simulation produced by the invention exhibited a precision at least equivalent to that of a reconstruction of the skin starting directly from images acquired by the imagery system.

The invention also relates to an imagery system, in particular of the MRI type, integrating hardware and software assets allowing the implementation of the process according to the invention, with these means originating in an obvious manner from the description of the process above. This system can, for example, comprise a magnetic resonance imaging device of the MAGNETOM Aera 1.5 Tesla type of the SIEMENS Company.

Of course, the invention is not limited to the embodiments described and shown in the accompanying drawings. Modifications remain possible, in particular from the standpoint of the composition of the various elements or by substitution of equivalent techniques, without thereby exceeding the field of protection of the invention.

The invention claimed is:

1. An automatic process of predictive determination, as a digital simulation, of a position and movements of skin of a human or animal subject in a zone of interest located at a level of a thorax or an abdomen, with said subject being stretched on said subject's back and breathing, said process comprising:
  in a preliminary phase, acquiring or determining multiple positions and configurations of a profile of the skin in predetermined, consecutive axial planes that are essentially perpendicular to the craniocaudal axis and distributed along the craniocaudal axis at determined locations, at given successive times, in different respiratory positions, during inhalation and exhalation phases of the subject,
  during a preliminary treatment phase, constructing at least one independent deformable digital model of the profile of the skin in each said axial plane (Pa) from data pertaining to different skin profiles (3) that are acquired or determined previously,
  noting, in a repetitive manner, an actual position of a point or a specific point zone (4) on the skin (2) of the subject (1) at the level of each of said axial planes (Pa), whose position is modified in a during the inhalation and exhalation phases, and
  providing, essentially in real time, a simulation (3') of the profile of the skin in each said axial plane (Pa), as a function of the actual position noted for each point or specific point zone (4) and by exploiting the deformable digital model of the skin profile in the corresponding axial plane (Pa), and, an evolving three-dimensional representation (2') of the skin (2) at the level of the zone of interest, this on the basis of a three-dimensional model for overall simulation of the skin composed of plural deformable and independent elementary two-dimensional axial models established in the axial planes (Pa) and by interpolation between said axial planes (Pa),
  wherein the points or specific point zones (4), whose actual position is monitored over time, are distributed along the craniocaudal axis by being aligned or not, with their number being at least equal 10 and their spacing of at most 5 cm in the direction of the craniocaudal axis.

2. Process according to claim 1, wherein the points or specific point zones (4) of the skin (2), whose actual position is monitored over time, are placed in a parallel plane that is close to or merged with the mid-sagittal plane (MSP) of the subject (1).

3. Process according to claim 1, further comprising, for each axial plane (Pa) in question, generating a curve (3') that represents the profile (3) of the skin (2) in the axial plane (Pa) in question by applying a deformation to a base curve (Cb) of the skin profile, determined in an end inhalation or exhalation state of the subject, by movement of at least points spaced on the base curve, based on the measured position of a point (4) on the skin (2) of the subject (1) located in the axial plane (Pa) in question.

4. Process according to claim 1, wherein each deformable digital model of the skin profile, respectively associated with one of the predetermined axial planes (Pa), is obtained by pairing points in an essentially radial direction, in the axial plane (Pa) in question, between at least two shapes or configurations that are different from the curve of the skin profile, corresponding to at least two different respective states of the respiratory movement of the subject.

5. Process according to claim 1, wherein each deformable digital model of the skin profile, associated with one of the predetermined axial planes (Pa), is obtained by generating a reference curve (Cr), located mid-way between the two skin profile curves corresponding to the end inhalation and exhalation states, to determine the intersection points, with the two skin profile curves, of a normal to the reference curve (Cr) and passing through a point of this curve, for a number of points spaced along the reference curve (Cr), and to assemble in an ordered manner these pairs of intersection points to constitute a deformation field corresponding to the movement of the skin (2) in the axial plane (Pa) in question between the end inhalation and exhalation states, as a function of the respiratory state of the subject (1).

6. Process according to claim 1, further comprising constructing two deformable digital models of the skin profile for each axial plane (Pa), namely a model for the inhalation phases and a model for the exhalation phases, and detecting the respiratory phase in progress during the production of simulated curves (3') of the skin profile in the different axial planes (Pa) by means of a specific sensor or by evaluating the direction of movement of the points (4).

7. Process according to claim 1, wherein the specific point positions (4) on the skin (2) are noted in real time by an optical sensor device, with or without preliminary installation of optical markers on the patient's skin (2) in the locations of specific points (4), with the latter being selected in such a way as to obtain a modification of their spatial position during the respiratory movement of the subject.

8. Process according to claim 1, wherein the positions of the points (4) of the skin (2) located in the mid-sagittal plane (MSP) of the subject (1) and in the predetermined axial planes (Pa) are determined by at least one marker (5).

9. Process according to claim 8, wherein the specific points (4) on the skin (2) are each highlighted by a marker (5) that is visible in the imagery process that is used, with these specific points (4) being located in such a way that their spatial position is modified during the respiratory movement of the subject.

10. Process according to claim 8, wherein the markers (5) that are used consist of electromagnetic-type markers resting on the skin (2).

11. Process according to claim 8, wherein the one marker (5) that is used comprises a continuously elongated marker, resting directly or indirectly on the skin (2) of the patient (1), conforming in shape to the local surface of the skin (2) and placed in the mid-sagittal plane (MSP).

12. Process according to claim 11, wherein the marker (5) that is used comprises a flexible and elongated body, made of a material that is visible in the imagery system that is used, extending at least over the length of the zone of interest in the direction of the craniocaudal axis (X), exhibiting a cross-section of determined minimal size and shape and located at a determined distance from the skin (2) of the subject (1), by resting on a strip (6) of a material that is flexible in the imagery system that is used.

13. Process according to claim 11, further comprising:
determining and noting, in the sagittal plane, the curve (Cm) corresponding to the median axis of the elongated marker (5), formed by the series of different centers of gravity in the cross-section of said marker (5), or in the different axial planes (Pa), the local centers of gravity of said marker (5), and
determining the positions of specific points (4) on the skin (2) of the subject (1) whose movements are taken into account, by exploiting the data pertaining, to this curve (Cm) or to these local centers of gravity, to the cross-section and to the cross-sectional dimensions of the marker (5), and to the thickness of the intermediate material strip (6).

14. Process according to claim 11, wherein when the imagery process to which the subject (1) is subjected is based on magnetic resonance, the elongated marker (5) comprises a bar formed by water gel, with a square or rectangular cross-section, and a sufficient length to cover at least the zone of the subject (1) whose movements induced by the breathing of said subject are to be monitored.

15. Process according to claim 1, wherein the curves showing the profile (3) of the skin (2) in spaced axial planes (Pa) that are predetermined and at different times for the inhalation and exhalation phases are extracted, by sampling along these axial planes, from three-dimensional representations of the surface of the skin (2) at the level of the zone of interest, acquired in advance and obtained by highlighting and monitoring the skin by markers attached to the skin or by structured light projected on the skin.

16. Process according to claim 1, wherein the curves showing the profile (3) of the skin (2) in spaced axial planes (Pa) that are predetermined and at different times for the inhalation and exhalation phases are extracted, by application of a segmentation technique, from three-dimensional representations obtained by an imagery process based on magnetic resonance or tomodensitometry.

17. Process according to claim 1, wherein the curves showing the profile (3) of the skin (2) in spaced axial planes (Pa) that are predetermined and at different times for the inhalation and exhalation phases are extracted, by segmentation, from 2D+t-type images made in said axial planes (Pa) and obtained by an imagery process based on magnetic resonance or tomodensitometry.

18. Process according to claim 1, wherein the evolving three-dimensional representation of the skin (2) at the level of the zone of interest is exploited, in connection with at least one three-dimensional image of the abdomen, for carrying out a predictive simulation in real time of the positions of the organs or viscera of the abdominal cavity during normal free breathing phases of the subject (1).

19. An automatic process of predictive determination, as a digital simulation, of a position and movements of skin of a human or animal subject in a zone of interest located at a level of a thorax or an abdomen, with said subject being stretched on said subject's back and breathing, said process comprising:
in a preliminary phase, acquiring or determining multiple positions and configurations of a profile of the skin in predetermined, consecutive axial planes that are essentially perpendicular to the craniocaudal axis and distributed along the craniocaudal axis at determined locations, at given successive times, in different respiratory positions, during inhalation and exhalation phases of the subject,
during a preliminary treatment phase, constructing at least one independent deformable digital model of the profile of the skin in each said axial plane (Pa) from data pertaining to different skin profiles (3) that are acquired or determined previously,
noting, in a repetitive manner, an actual position of a point or a specific point zone (4) on the skin (2) of the subject (1) at the level of each of said axial planes (Pa), whose position is modified in a during the inhalation and exhalation phases, and
providing, essentially in real time, a simulation (3') of the profile of the skin in each said axial plane (Pa), as a function of the actual position noted for each point or specific point zone (4) and by exploiting the deformable digital model of the skin profile in the corresponding axial plane (Pa), and, an evolving three-dimensional representation (2') of the skin (2) at the level of the zone of interest, this on the basis of a three-dimensional model for overall simulation of the skin composed of plural deformable and independent elementary two-dimensional axial models established in the axial planes (Pa) and by interpolation between said axial planes (Pa),
wherein each deformable digital model of the skin profile, respectively associated with one of the predetermined axial planes (Pa), is obtained by pairing points in an essentially radial direction, in the axial plane (Pa) in question, between at least two shapes or configurations that are different from the curve of the skin profile, corresponding to at least two different respective states of the respiratory movement of the subject.

20. An automatic process of predictive determination, as a digital simulation, of a position and movements of skin of a human or animal subject in a zone of interest located at a level of a thorax or an abdomen, with said subject being stretched on said subject's back and breathing, said process comprising:

in a preliminary phase, acquiring or determining multiple positions and configurations of a profile of the skin in predetermined, consecutive axial planes that are essentially perpendicular to the craniocaudal axis and distributed along the craniocaudal axis at determined locations, at given successive times, in different respiratory positions, during inhalation and exhalation phases of the subject, during a preliminary treatment phase, constructing at least one independent deformable digital model of the profile of the skin in each said axial plane (Pa) from data pertaining to different skin profiles (3) that are acquired or determined previously, noting, in a repetitive manner, an actual position of a point or a specific point zone (4) on the skin (2) of the subject (1) at the level of each of said axial planes (Pa), whose position is modified in a during the inhalation and exhalation phases, and providing, essentially in real time, a simulation (3') of the profile of the skin in each said axial plane (Pa), as a function of the actual position noted for each point or specific point zone (4) and by exploiting the deformable digital model of the skin profile in the corresponding axial plane (Pa), and, an evolving three-dimensional representation (2') of the skin (2) at the level of the zone of interest, this on the basis of a three-dimensional model for overall simulation of the skin composed of plural deformable and independent elementary two-dimensional axial models established in the axial planes (Pa) and by interpolation between said axial planes (Pa), wherein each deformable digital model of the skin profile, associated with one of the predetermined axial planes (Pa), is obtained by generating a reference curve (Cr), located mid-way between the two skin profile curves corresponding to the end inhalation and exhalation states, to determine the intersection points, with the two skin profile curves, of a normal to the reference curve (Cr) and passing through a point of the reference curve (Cr), for a number of points spaced along the reference curve (Cr), and to assemble in an ordered manner these pairs of intersection points to constitute a deformation field corresponding to the movement of the skin (2) in the axial plane (Pa) in question between the end inhalation and exhalation end states, as a function of the respiratory state of the subject (1).

* * * * *